(12) United States Patent
Nuernberger

(10) Patent No.: US 9,248,226 B2
(45) Date of Patent: Feb. 2, 2016

(54) DEVICE AND METHOD FOR DETECTING THE RECIRCULATION DURING AN EXTRACORPOREAL BLOOD TREATMENT

(71) Applicant: Fresenius Medical Care Deutschland GmbH, Bad Homburg v.d.H. (DE)

(72) Inventor: Thomas Nuernberger, Burkadroth (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 314 days.

(21) Appl. No.: 14/032,922

(22) Filed: Sep. 20, 2013

(65) Prior Publication Data

US 2014/0083943 A1  Mar. 27, 2014

Related U.S. Application Data

(60) Provisional application No. 61/703,845, filed on Sep. 21, 2012.

(30) Foreign Application Priority Data

Sep. 21, 2012  (DE) .......................... 10 2012 018 628

(51) Int. Cl.
| | |
|---|---|
| *C02F 1/00* | (2006.01) |
| *A61M 1/36* | (2006.01) |
| *A61M 1/16* | (2006.01) |
| *A61M 1/34* | (2006.01) |

(52) U.S. Cl.
CPC ........... *A61M 1/3663* (2013.01); *A61M 1/1656* (2013.01); *A61M 1/3431* (2014.02); *A61M 1/3653* (2013.01); *A61M 1/3656* (2014.02); *A61M 1/3658* (2014.02); *A61M 1/342* (2013.01);

(Continued)

(58) Field of Classification Search
USPC ........................................... 210/90, 101, 646
See application file for complete search history.

(56) References Cited

U.S. PATENT DOCUMENTS

| 5,830,365 A | 11/1998 | Schneditz |
| 6,117,099 A | 9/2000 | Steuer et al. |

FOREIGN PATENT DOCUMENTS

| DE | 102008003714 A1 | 7/2009 |
| EP | 1 595 560 A1 | 11/2005 |
| WO | WO98/32477 A1 | 7/1998 |

OTHER PUBLICATIONS

International Search Report dated Nov. 4, 2013 from PCT/EP2013/002718.

(Continued)

*Primary Examiner* — Dirk Bass
(74) *Attorney, Agent, or Firm* — Kenyon & Kenyon LLP

(57) ABSTRACT

A device and method for detecting recirculation for an extracorporeal blood treatment apparatus and an apparatus with a device for detecting recirculation are based on targeted haemodilution by administration of a substituate bolus, causing a pressure change in venous and arterial branches of the extracorporeal circuit due to a viscosity change of flowing fluid. Recirculation is detected based on detection of the pressure change. The device includes a control unit cooperating with a device for conveying blood and a device for supplying substituate. The control unit provides an operating mode for detecting recirculation, in which blood flow rate is reduced during administration of a substituate bolus. With simultaneous substituate bolus administration and reduction of blood flow rate, the composition of fluid flow is optimized for detection of recirculation, so that fairly large pressure changes result in venous and arterial branches, thereby improving sensitivity and reliability of the measurement method.

16 Claims, 3 Drawing Sheets

(52) U.S. Cl.
CPC ...... *A61M 1/3639* (2013.01); *A61M 2205/3331* (2013.01); *A61M 2205/3334* (2013.01)

(56) References Cited

OTHER PUBLICATIONS

Schneditz, D., et al., "Cardiopulmonary recirculation during haemodialysis," Kidney Int. 42: 1450-1456, 1992.

Bay, W., et al., "Color Doppler flow predicts PTFE graft failure," J. Am. Soc. Nephrol. 5:407 1994.

Gotch, F., "Models to predict recirculation and its effects on treatment time in single-needle-dialysis," First Intl. Symposium on Single-Needle-Dialysis, S. Rignoir, R. Vanholder and P. Ivanovich, Cleveland, ISAO Press, 1984, p. 305 ff.

International Preliminary Report on Patentability dated Mar. 24, 2015 in PCT/EP2013/002718.

DEVICE AND METHOD FOR DETECTING THE RECIRCULATION DURING AN EXTRACORPOREAL BLOOD TREATMENT

CROSS REFERENCE TO RELATED APPLICATIONS

The present application claims priority to U.S. Provisional Patent Application No. 61/703,845, filed on Sep. 21, 2012, and claims priority to Application No. DE 10 2012 018 628.2, filed in the Federal Republic of Germany on Sep. 21, 2012, each of which is expressly incorporated herein in its entirety by reference thereto.

FIELD OF INVENTION

The present invention relates to a device for detecting the recirculation for an extracorporeal blood treatment apparatus as well as an extracorporeal blood apparatus with a device for detecting the recirculation. Moreover, the present invention relates to a method for detecting the recirculation during an extracorporeal blood treatment.

BACKGROUND INFORMATION

Various methods for extracorporeal blood treatment or cleaning are used to remove substances usually eliminated with urine and for fluid withdrawal. In haemodialysis, the patient's blood is cleaned outside the body in a dialyser. The dialyser comprises a blood chamber and a dialysing fluid chamber, which are separated by a semipermeable membrane. During the treatment, the patient's blood flows through the blood chamber. In order to clean the blood effectively from substances usually eliminated with urine, fresh dialysing fluid flows continuously through the dialysing fluid chamber.

Whereas the transport of the lower-molecular substances through the membrane of the dialyser is essentially determined by the concentration differences (diffusion) between the dialysing fluid and the blood in the case of haemodialysis (HD), substances dissolved in the plasma water, in particular higher-molecular substances, are effectively removed by a high fluid flow (convection) through the membrane of the dialyser in the case of haemofiltration (HF). In haemofiltration, the dialyser functions as a filter. Haemodiafiltration (HDF) is a combination of the two processes.

In haemo(dia)filtration, a part of the fluid removed from the blood through the membrane of the dialyser is replaced by a sterile substitution fluid, which is generally fed to the extracorporeal blood circuit either upstream of the dialyser or downstream of the dialyser.

The supply of substitution fluid upstream of the dialyser is also referred to as pre-dilution and the supply downstream of the dialyser as post-dilution.

Apparatuses for haemo(dia)filtration are known, wherein the dialysing fluid is prepared online from fresh water and concentrations and the substitution fluid is prepared online from the dialysing fluid.

In the known haemo(dia)filtration apparatuses, the substitution fluid (substituate) is fed to the extracorporeal blood circuit from the fluid system of the machine via a substituate line. With pre-dilution, the substituate line leads to a connection point on the arterial blood line upstream of the dialyser or filter, whereas with post-dilution the substituate line leads to a connection point on the venous blood line downstream of the dialyser or filter.

With the known methods of chronic blood cleaning therapy, such as haemodialysis, haemofiltration and haemodiafiltration, the vascular connection (shunt) is generally applied between an artery and vein in operative surgery as an access to the patient's blood vessel system. When mention is made in the following of a "fistula", this is understood to mean any kind of connection between a vein and an artery of the patient.

The blood flowing through the fistula is used only during the actual dialysis treatment. In the period free from dialysis, the blood flow in the fistula corresponds to a functional left/right shunt, wherein a part of the arterial blood is fed from the heart minute volume (HMV), bypassing a peripheral use, directly to the venous system and the heart. The fistula flow recirculates via the heart and lungs. The fractional part of the fistula flow in the heart minute volume is defined as the cardiopulmonary recirculation.

The cardiopulmonary recirculation not only has effects on the patient's circulatory load, but also on the efficiency of the dialysis. Since the dialysed blood from the extracorporeal circuit is mixed with the venous backflow from the large body circulation thereby bypassing the systemic circulatory areas, a systematic reduction in the concentration of the dialysable constituents in the arterial blood results (D. Schneditz et al., Cardiopulmonary recirculation during haemodialysis, Kidney Int. 42: 1450-1456, 1992).

Of importance for the functional capability of the fistula is its perfusion. If the fistula flow falls below a critical value, the risk of a fistula thrombosis then increases with the possible loss of the vascular access, which in dialysis treatment represents a considerable complication (W. Bay et al., Color Doppler flow predicts PTFE graft failure, J. Am. Soc. Nephrol. 5: 407 (1994)). If the fistula flow during the dialysis treatment is smaller than the extracorporeal blood flow ($Q_B$), local fistula recirculation occurs, wherein a fraction of the dialysed blood fed back to the fistula with the venous blood line is again fed to the dialyser via the arterial blood line. Fistula recirculation $R_A$ causes a significant reduction in the dialysis efficiency (F. Gotch, "Models to predict recirculation and its effects on treatment time in single-needle-dialysis," First Intl. Symposium on Single-Needle-Dialysis, S. Rignoir, R. Vanholder and P. Ivanovich, Cleveland, ISAO Press, 1984, page 305 ff.). The measurement of the quality of the vascular access is therefore an important means of quality assurance in dialysis treatment.

International Patent Publication No. WO 98/32477 describes a method for measuring recirculation R, i.e., the sum of the fistula recirculation ($R_A$) and the cardiopulmonary recirculation $R_{CP}$. With the known method, a physical or chemical characteristic variable of the dialysing fluid is changed in the dialysing fluid path upstream of the dialyser, which leads to a change in the physical or chemical characteristic variable on the blood side. The change in the characteristic variable on the blood side leads to a change in the characteristic variable of the dialysing fluid downstream of the dialysing fluid chamber of the dialyser. In order to determine the recirculation, the characteristic variable in the dialysing fluid path downstream of the dialyser is measured and recirculation R is determined from the time-related course of the change in the characteristic variable. The dialysing fluid ion concentration, for example the Na concentration of the dialysing fluid, or the temperature of the dialysing fluid, can be changed and measured as a physical or chemical characteristic variable.

U.S. Pat. No. 5,830,365 describes a method for determining the cardiopulmonary recirculation, which is based on two measurements of the recirculation fraction following shortly after one another, which are carried out automatically before and after the reversal of the blood flow. The drawback is that the known method requires the reversal of the blood flow.

European Application No. EP 1 595 560 describes a method for determining the recirculation, wherein the viscosity of the blood in the arterial or venous blood line is changed by switching on and/or switching off the substitute pump. The change in the viscosity of the blood leads to a drop in pressure or rise in pressure on the venous or arterial side of the extracorporeal blood circuit, which is picked up in order to detect a recirculation on the basis of the change in pressure. The known method provides for a change in the substitute rate by switching on and/or switching off the substitute pump, whilst the blood pump in the extracorporeal blood circuit continues to convey blood at the preset blood flow rate.

SUMMARY

A problem underlying the present invention is to provide a device with which a recirculation can be detected quickly and reliably during an extracorporeal blood treatment, so that the checking of the state of the fistula during the extracorporeal blood treatment can be carried out routinely without great expense.

The device according to the present invention and the method according to the present invention are based on a targeted haemodilution by the administration of a bolus of a substitution fluid (substitute). Due to a change in the viscosity of the fluid flowing in the extracorporeal circuit, the haemodilution leads to a change in the pressure conditions in the venous and arterial branch of the extracorporeal blood circuit. A recirculation is detected on the basis of the detection of the change in pressure in the extracorporeal circuit. The change in pressure can appear as an increase of the pressure in the arterial blood line or a reduction of the pressure in the venous blood line.

The device according to the present invention and the method according to the present invention are characterised by a targeted reduction in the blood flow rate during the administration of the bolus of substitute. During the extracorporeal blood treatment, the blood flow rate within a preset time interval is reduced from a preset current blood flow rate, which is referred to below as the first blood flow rate, to a blood flow rate which is referred to below as the second blood flow rate. The second blood flow rate preferably corresponds to a minimum blood flow rate, which can be preset by the doctor. According to the present invention, the reduction in the blood flow rate is compensated again at least partially by the bolus administration of substitute. The reduced volume of blood in the preset time interval is preferably replaced completely by substitute. The bolus administration should take place simultaneously with the reduction in the blood flow rate, i.e., the preset time interval, in which the blood treatment takes place with a reduced blood flow rate, should correspond to the time interval in which the substitute bolus is administered. Certain time shifts between the time intervals of the reduction in the blood flow rate and the bolus administration can however also be preset.

It has been shown that, with the simultaneous bolus administration of substitute and the reduction of the blood flow rate, the composition of the fluid flowing through the extracorporeal circuit, i.e., the blood diluted with substitute, is optimised for the detection of a recirculation. From the targeted change in the blood flow rate and substitute rate within the time interval, fairly large pressure changes result in the venous and arterial branch of the extracorporeal circuit, which can be picked up with a high degree of reliability for the detection of a recirculation. The sensitivity and reliability of the measurement method are thus improved overall.

The device according to the present invention for the detection of the recirculation can form a separate assembly or can be a component of the extracorporeal blood treatment apparatus.

The device according to the present invention for the detection of the recirculation is preferably a component of the blood treatment apparatus, which already comprises the main components for performing the method according to the present invention.

The device for determining the recirculation comprises a measuring unit for measuring the pressure in the extracorporeal circuit in the arterial and/or venous blood line and an evaluation unit for detecting the recirculation on the basis of the pressure measurement. Moreover, the device for detecting the recirculation comprises a control unit, which cooperates with the device for conveying blood to the blood treatment apparatus and the device for supplying substitute to the blood treatment apparatus. The control unit provides an operating mode for detecting the recirculation, in which the device for conveying blood is controlled such that preset first blood flow rate $Q_{b1}$ is reduced to second blood flow rate $Q_{b2}$ in a preset time interval, and the device for supplying substitute is controlled such that substitute is supplied in the preset time interval at a preset substitute rate $Q_s$ to the blood in the arterial blood line upstream of the dialyser or filter. The conveying rates can be constant or have a specific profile, for example rise and fall continuously or discontinuously, within the preset time interval.

In a preferred exemplary embodiment, the control unit is constituted such that the device for supplying substitute in the preset time interval in the operating mode for detecting the recirculation is controlled such that the difference between preset substitute rate $Q_s$ and the difference between first blood flow rate $Q_{b1}$ and second blood flow rate $Q_{b2}$ corresponds to a specific value. The reduction in the blood flow rate is thus at least partially compensated for by the supply of substitute. Preferably, however, the specific value is zero, so that a complete compensation takes place.

A particularly preferred exemplary embodiment makes provision such that the evaluation unit generates a control signal signalling the presence of a recirculation when a pressure change is detected, wherein the device for determining the recirculation comprises an optical and/or acoustic signal unit receiving the control signal of the evaluation unit, said signal unit generating an acoustic and/or optical signal when the signal unit receives the control signal from the evaluation unit.

A pressure drop in the venous branch of the extracorporeal blood circuit first arises on account of the haemodilution due to the bolus administration with the reduction in the blood flow. If a recirculation is present, a part of the blood volume passes directly into the arterial branch of the blood circuit, which leads to a time-shifted pressure rise in the arterial branch of the blood circuit, since the pressure drop at the arterial cannula is reduced on account of the reduction in the viscosity. The recirculation can consequently be detected by a pressure rise in the arterial branch of the blood circuit.

In a particularly preferred exemplary embodiment, the evaluation unit is constituted such that the amount of the change in pressure in the arterial or venous blood line is compared with a preset threshold value, wherein the evaluation unit generates a control signal indicating the presence of a recirculation when the amount of the change in pressure is greater than the preset threshold value. Other evaluation methods can however also be used to detect a recirculation. The only important point is that the pressure rise due to the recirculation is detected.

In general, it is sufficient when a recirculation is detected for information to be obtained concerning the state of the vascular access. The device according to the present invention for detecting the recirculation, however, also permits a determination of the recirculation. For the calculation of the percentage fraction of the recirculation, the evaluation unit is preferably constituted such that the ratio between the amount of the change in the pressure measured in the arterial blood line and the pressure measured in the venous blood line is calculated. The integrals of the pressure signals measured with the pressure measuring units are preferably put into a relationship with one another.

The recirculation can also be precisely determined with the other methods known in the prior art, as soon as the device according to the present invention has detected a recirculation.

For the rapid initiation of a recirculation test, a further particularly preferred exemplary embodiment provides an actuation unit for the control unit, which is constituted such that, after actuation of an actuation element, the control unit selects the operating mode for detecting the recirculation, so that the process steps required for this are carried out automatically. The recirculation test can thus be initiated quickly and then carried out automatically. The actuation unit can be a mechanical switch or pushbutton or an operator panel of a touch-screen.

Exemplary embodiments of the present invention are explained in detail below with reference to the accompanying drawings.

DETAILED DESCRIPTION

Figure 1:
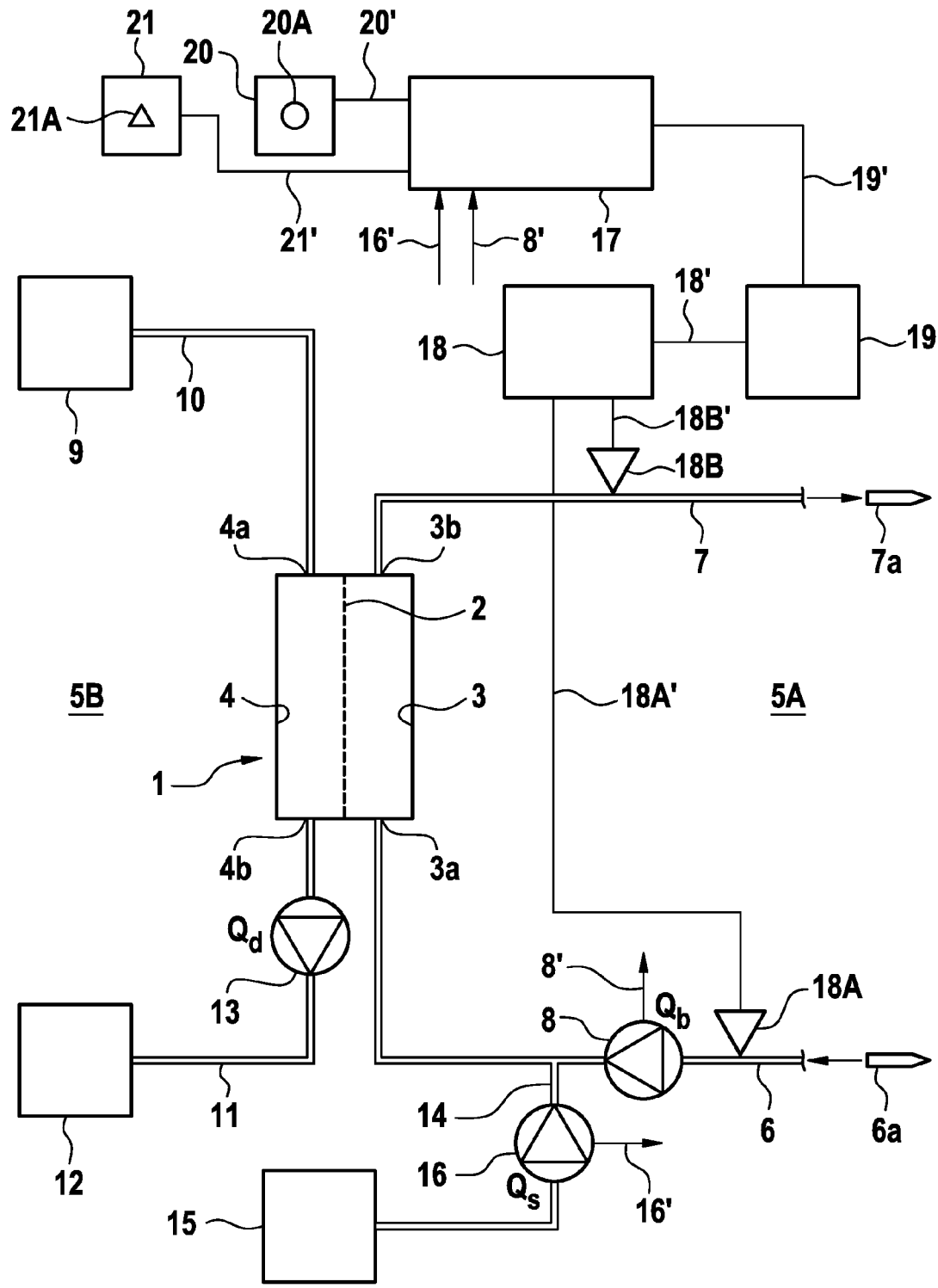
FIG. 1 shows an extracorporeal blood treatment apparatus with a device for detecting the recirculation in a very simplified diagrammatic representation.

FIG. 1 shows in a simplified diagrammatic representation only the main components of an extracorporeal blood treatment apparatus, which comprises a device for detecting the recirculation.

The present blood treatment apparatus is a haemo(dia) filtration apparatus, which comprises a dialyser 1, which is separated by a semipermeable membrane 2 into a first chamber 3 through which blood flows, which is referred to in the following as a blood chamber, and a second chamber 4 through which dialysing fluid flows, which is referred to as a dialyser fluid chamber. First chamber 3 is incorporated into an extracorporeal blood circuit 5A, whilst second chamber 4 is incorporated into dialysing fluid system 5B of the haemo(dia) filtration apparatus.

Extracorporeal blood circuit 5A comprises an arterial blood line 6, which leads from an arterial cannula 6a to inlet 3a of blood chamber 3, and a venous blood line 7, which leads away from outlet 3b of blood chamber 3 of dialyser 1 and leads to a venous cannula 7a. The arterial and venous cannulas are connected to the fistula (shunt) of the patient, said fistula not being represented. The patient's blood is delivered through blood chamber 3 of dialyser 1 by an arterial blood pump 8, which is disposed on arterial blood line 6. Blood pump 8 feeds blood at a preset blood flow rate $Q_b$, referred to as the first blood flow rate, to blood chamber 3 of the dialyser. The first blood flow rate can be changed during the blood treatment. Blood lines 6, 7 and dialyser 1 form a disposable intended for one-off use, which is inserted into the dialysis apparatus for the dialysis treatment. In order to eliminate air bubbles, air separators (drip chambers) can be incorporated into the arterial and venous blood line.

The fresh dialysing fluid is prepared in a dialysing fluid source 9. From dialysing fluid source 9, a dialysing fluid supply line 10 leads to inlet 4a of dialysing fluid chamber 4 of dialyser 1. A dialysing fluid discharge line 11 leads from outlet 4b of dialysing fluid chamber 4 to a drain 12. A dialysing fluid pump 13 is incorporated into dialysing fluid discharge line 11.

During the dialysis treatment, substitution fluid (substituate) can be fed from a substituate source 15 via a substituate line 14 to extracorporeal blood circuit 5A. Substitution line 14 is connected to a line segment of arterial blood line 6 downstream of blood pump 8 and upstream of blood chamber 3 of dialyser 1. The substituate is conveyed with a substituate pump 16, which feeds substituate at a preset substituate rate $Q_s$ to arterial blood line 6. The substituate can be a fluid prepared from the dialysing fluid during the treatment. The substituate can however also be a fluid prepared in the substituate source, for example a cooking salt solution.

The device for detecting a recirculation comprises a control unit 17, which can be a component of the central control and computing unit of the blood treatment apparatus. Blood pump 8 and substituate pump 16 are connected via control lines 8', 16' to control unit 17 of the device for detecting the recirculation. The control unit switches pumps 8, 16 on and off and presets specific flow rates for the pumps.

Moreover, the device for detecting the recirculation comprises a measuring unit 18 with an arterial pressure sensor 18A for measuring the pressure in arterial blood line 6 upstream of blood pump 8 and a venous pressure sensor 18B for measuring the pressure in venous blood line 7 downstream of the blood chamber of the dialyser. Arterial and venous pressure sensors 18A, 18B are connected via data lines 18A', 18B' to measuring unit 18, and measuring unit 18 is connected via a data line 18' to an evaluation unit 19 of the device for detecting a recirculation, said evaluation unit being connected via a data line 19' again to control unit 17.

Furthermore, the device for detecting the recirculation comprises an actuation unit 20 with an actuation element 20A, for example a pushbutton, and a signal unit 21, which comprises an optical and/or acoustic signal transmitter 21A. Actuation unit 20 and signal unit 21, which can also be a component of the blood treatment apparatus, are connected via control and data lines 20', 21' to control unit 17.

Control unit 17 can be a data processing unit (microprocessor), on which a data processing program runs in order to execute the steps required for the performance of the method according to the present invention. The mode of functioning of the control unit is described in detail below. The control unit is configured (programmed) such that the individual components of the blood treatment apparatus are controlled as follows.

During the blood treatment, blood pump 8 conveys the blood at a preset first blood flow rate $Q_{b1}$, which can vary during the blood treatment. To initiate the recirculation test, actuation element 20A is actuated, for example the pushbutton is pressed. After pressing of the pushbutton, control unit 17 selects the operating mode for detecting the recirculation, so that blood pump 8 and substitute pump 16 are controlled for the administration of a substitute bolus with a reduced blood flow. Control unit 17 is configured (programmed) such that blood pump 8 conveys the blood within a preset time interval $\Delta T$ at a reduced second blood flow rate $Q_{b2}$. Control unit 17 calculates the difference between first blood flow rate $Q_{b1}$ and second blood flow rate $Q_{b2}$ and presets a rate for substitute rate $Q_s$ which corresponds to the difference between first and second blood flow rates $Q_{b1}$, $Q_{b2}$.

Figure 2:
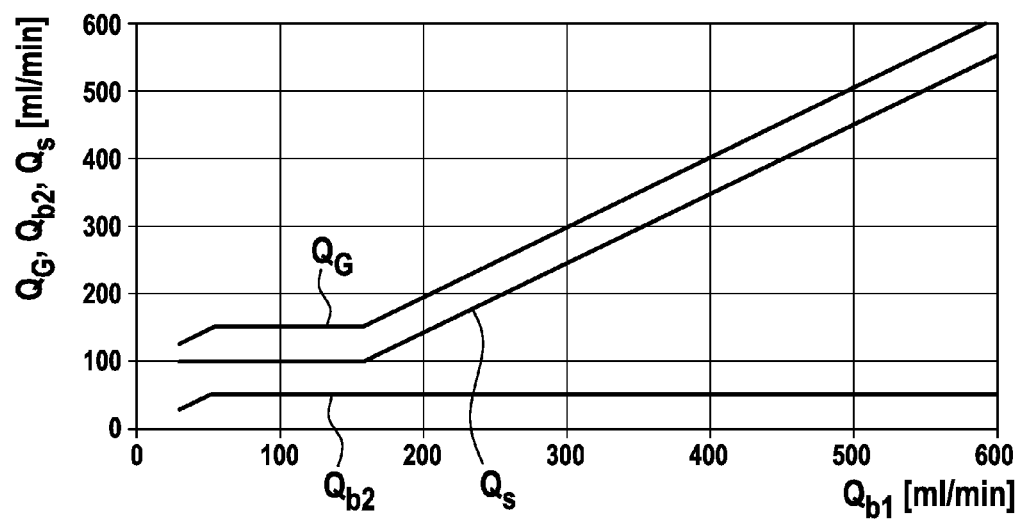
FIG. 2 shows a diagram to illustrate the flow rates in the extracorporeal blood circuit during the bolus administration.

FIG. 2 illustrates the selection of substitute rate $Q_s$ during the bolus administration for different flow rates. The blood flow rate is reduced from a value $Q_{b1}$ to a minimum value $Q_{b2}=Q_{min}$, for example 50 ml/min. For a blood flow rate $Q_{b1}$ before the bolus administration of 400 ml/min, a value of 350 ml/min results for example for substitute rate $Q_s$ during the bolus administration, from which the value of 400 ml again results as the sum $Q_G=Q_s+Q_{b2}$.

In the operating mode for recirculation detection, arterial and venous pressure sensor 18A, 18B of measuring unit 18 measures the pressure in arterial and venous blood line 6, 7, wherein evaluation unit 19 evaluates the pressure signals.

Figure 3:
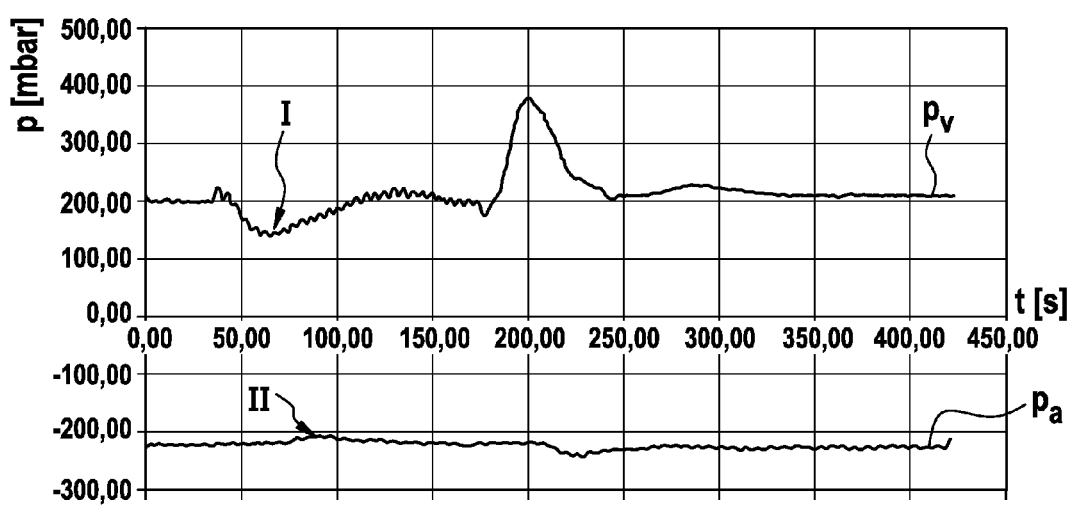
FIG. 3 shows a first exemplary embodiment of the time-related course of the pressure in the arterial and venous branch of the extracorporeal blood circuit during the bolus administration in the presence of a recirculation.
Figure 4:
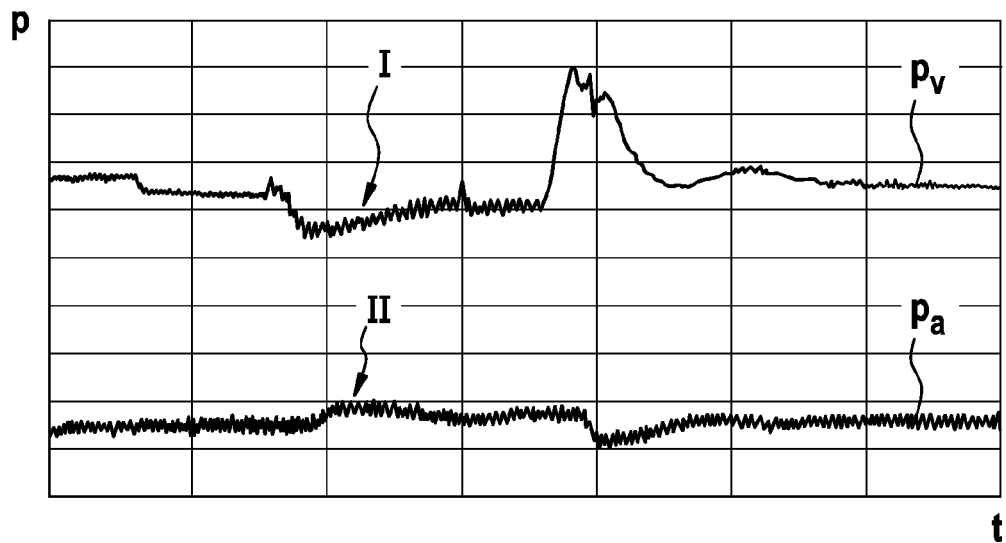
FIG. 4 shows a second exemplary embodiment of the time-related course of the pressure in the arterial and venous branch of the extracorporeal blood circuit during the bolus administration in the presence of a recirculation.
Figure 5:
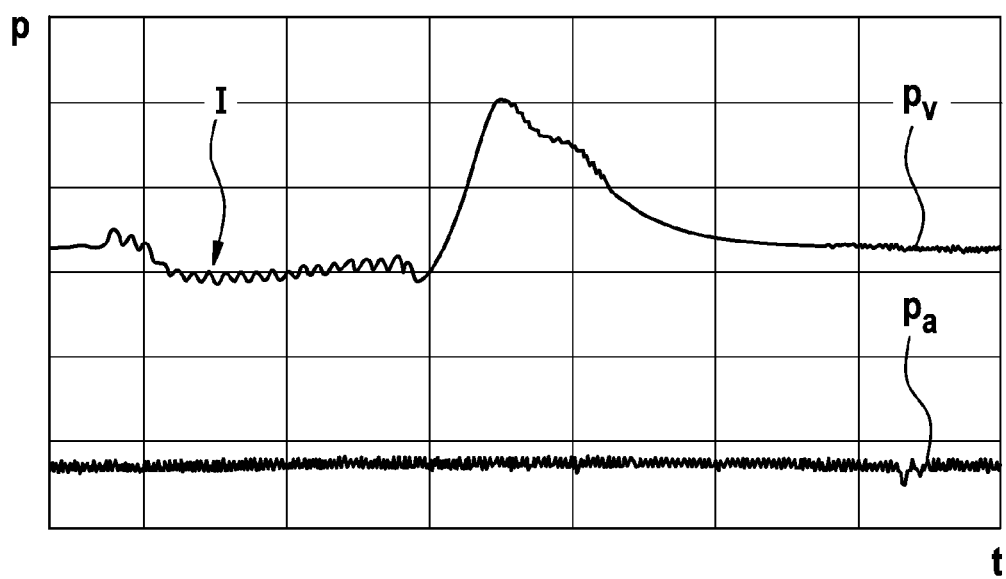
FIG. 5 shows the time-related course of the pressure in the arterial and venous branch of the extracorporeal blood circuit during the bolus administration when no recirculation is taking place.

FIG. 3 shows the measured time-related course of venous and arterial pressure $p_v$ (mbar) and $p_a$ (mbar). After the substituate bolus with a reduced blood flow, a pressure drop I by a specific amount is detected in venous blood line 7 and a pressure rise II is detected in arterial blood line 6 on account of the haemodilution, the latter being denoted by the symbols I and II. In this exemplary embodiment, the recirculation amounts to 20%. For comparison, FIG. 4 shows the time-related course of venous and arterial pressure $p_v$ (mbar) and $p_a$ (mbar) with a recirculation of 40%, whilst FIG. 5 shows the time-related course of venous and arterial pressure $p_v$ (mbar) and $p_a$ (mbar) when no recirculation is present. It can clearly be seen that an arterial pressure rise can be noted only in the case of the recirculation.

The characteristic course of the pressure signal shown in FIGS. 3 to 5 is due to the changed viscosity of the blood. On account of the bolus administration, the viscosity of the blood in venous blood line 7 downstream of the blood chamber is increased on account of the supply of substitute. Consequently, a smaller pressure drop occurs at venous cannula 7a. The venous pressure thus drops. After the bolus administration, the viscosity of the blood in venous blood line 7 is reduced again, so that the venous pressure increases again. On account of the fistula recirculation, a part of the diluted blood passes via the fistula directly into arterial blood line 6, which leads to a reduction in viscosity, for which reason the pressure in the arterial blood line increases. Evaluation unit 19 concludes from the arterial pressure rise or venous pressure drop that a fistula recirculation is present. In this regard, evaluation unit 19 determines the amount of the pressure rise in arterial blood line 6 and compares the amount with a preset threshold value. Alternatively, evaluation unit 19 can also determine the amount of the pressure drop in venous blood line 7 and compares the amount with a preset threshold value. If the threshold value is exceeded with a significant change in the pressure, evaluation unit 19 generates a control signal which signals a recirculation. Signal unit 21 receives the control signal of evaluation unit 19 via control unit 17, so that signal transmitter 21A generates an acoustic and/or optical alarm. The doctor performing treatment can then take the necessary measures.

The device according to the present invention also permits the determination of the recirculation. The ratio between the amount of the maximum change in the arterial pressure signal of the arterial pressure sensor and the amount of the maximum change in the venous pressure signal of the venous pressure sensor serves as a measure for the recirculation. The recirculation Rez [%] is calculated by the evaluation unit according to the following equation.

The relationship between the obtained haematocrit change $\Delta Hkt$ and the measured pressure change ($\Delta p_a$ and $\Delta p_v$) on the venous and arterial side is however not linear. Moreover, there is a dependence on blood flow $Q_b$, the geometry of the cannula, in particular its diameter, and the absolute haematocrit value. The device according to the present invention therefore preferably provides for a measurement under defined conditions, wherein $Q_b$ and $Q_s$ are constant, so that the recirculation Rez [%] can be determined according to the above equation with sufficient accuracy.

In contrast with a measurement on the basis of a thickening instead of a thinning of the blood, the problem does not arise that the dialyser may become clogged up or blood clots may form in the hose system. Moreover, no effects from the cardiopulmonary recirculation on the measurement result appear with the measurement method according to the present invention due to the detection of the pressure change immediately after the haemodilution.

What is claimed is:

1. A device for detecting recirculation for an extracorporeal blood treatment apparatus, the extracorporeal blood treatment apparatus comprising an extracorporeal blood circuit with an arterial blood line, which leads to a first chamber of a dialyser or filter divided by a membrane into the first chamber and a second chamber, and a venous blood line, which leads away from the first chamber of the dialyser or filter, a device for conveying blood at a preset blood flow rate $Q_b$ through the arterial blood line into the first chamber of the dialyser or filter and through the venous blood line from the first chamber of the dialyser or filter, and a device for supplying substituate to the blood at a preset substituate rate $Q_s$ in the arterial blood line upstream of the dialyser or filter, the device for detecting the recirculation comprising:

A measuring unit adapted for measuring pressure in the extracorporeal circuit in the arterial and/or venous blood line;

An evaluation unit adapted for detecting the recirculation based on the pressure measurement; and A control unit cooperating with the device for conveying blood and the device for supplying substituate, the control unit being adapted, in an operating mode for detecting the recirculation, to control the device for conveying blood such that in a preset time interval, a preset first blood flow rate $Q_{b1}$ is reduced to a preset second blood flow rate $Q_{b2}$, and to control the device for supplying substituate such that in the preset time interval, substituate is fed at the preset substituate rate $Q_s$ to the blood in the arterial blood line upstream of the dialyser or filter, wherein the evaluation unit is adapted to monitor the pressure measured by the measuring unit in the arterial and/or venous blood line for a change in the pressure and to compare an amount of the change in the pressure in the arterial and/or venous blood line with a preset threshold value, wherein the evaluation unit generates a control signal indicating a presence of the recirculation when the amount of the pressure change is greater than the preset threshold value.

2. The device according to claim 1, wherein the evaluation unit is adapted to generate a control signal signalling a presence of the recirculation when a pressure increase is detected in the arterial blood line.

3. The device according to claim 1, wherein the evaluation unit is adapted to generate a control signal signalling a presence of the recirculation when a pressure reduction is detected in the venous blood line.

4. The device according to claim 1, further comprising:
an optical and/or acoustic signal unit adapted to receive a control signal of the evaluation unit, said signal unit being adapted to generate an acoustic and/or optical signal when the signal unit receives the control signal from the evaluation unit.

5. The device according to claim 1, wherein the control unit is adapted to control the device for supplying substitute in the preset time interval in the operating mode for detecting the recirculation such that a difference between the preset substitute rate $Q_s$ and a difference between the first blood flow rate $Q_{b1}$ and the second blood flow rate $Q_{b2}$ corresponds to a specific value.

6. The device according to claim 5, wherein the specific value is zero.

7. The device according to claim 1, wherein the evaluation unit is adapted to calculate a ratio between an amount of the change in the pressure measured by the measuring unit in the arterial blood line and an amount of the change in the pressure measured in the venous blood line.

8. The device according to claim 1, further comprising:
an actuation unit provided for the control unit, the actuation unit being adapted such that, after actuation of an actuation element, the control unit selects the operating mode for detecting the recirculation, in which the device for conveying blood and the device for supplying substituate are controlled.

9. An extracorporeal blood treatment apparatus, comprising:
an extracorporeal blood circuit with an arterial blood line, which leads to a first chamber of a dialyser or filter divided by a membrane into the first chamber and a second chamber, and a venous blood line, which leads away from the first chamber of the dialyser or filter,
a fluid system, which comprises the second chamber of the dialyser or filter,
a device for conveying blood at a preset blood flow rate $Q_b$ through the arterial blood line into the first chamber of the dialyser or filter and through the venous blood line from the first chamber of the dialyser or filter,
a device for supplying substitute to the blood at a preset substituate rate $Q_s$ in the arterial blood line upstream of the dialyser or filter, and
the device for detecting the recirculation according to claim 1.

10. A method for detecting recirculation for an extracorporeal blood treatment apparatus, the extracorporeal blood treatment apparatus comprising an extracorporeal blood circuit with an arterial blood line, which leads to a first chamber of a dialyser or filter divided by a membrane into the first chamber and a second chamber, and a venous blood line which leads away from the first chamber of the dialyser or filter, a fluid system, which comprises the second chamber of the dialyser or filter, a device for conveying blood at a preset blood flow rate $Q_b$ through the arterial blood line into the first chamber of the dialyser or filter and through the venous blood line from the first chamber of the dialyser or filter, a device for supplying substitute to the blood at a preset substitute rate $Q_s$ in the arterial blood line upstream of the dialyser or filter, wherein pressure in the extracorporeal blood circuit is measured in the arterial and/or venous blood line and detection of the recirculation takes place based on the pressure measurement, the method comprising:

In an operating mode for detecting the recirculation,
Reducing a preset first blood flow rate $Q_{b1}$ to a preset second blood flow rate $Q_{b2}$ in a preset time interval,
Supplying substitute at the preset substituate rate $Q_s$ to the blood in the arterial blood line upstream of the dialyser or filter in the preset time interval,
Monitoring the pressure measured by a measuring unit in the arterial and/or venous blood line for a change in the pressure, and
Detecting a presence of the recirculation by comparing an amount of the change in the pressure in the arterial and/or venous blood line with a preset threshold value, wherein the presence of the recirculation is detected when the amount of the change in pressure is greater than the preset threshold value.

11. The method according to claim 10, wherein the pressure measured by the measuring unit in the arterial blood line is monitored for an increase in the pressure, wherein the presence of the recirculation is detected when there is an increase in pressure.

12. The method according to claim 10, wherein the pressure measured by the measuring unit in the venous blood line is monitored for a reduction in the pressure, wherein the presence of the recirculation is detected when there is a reduction in pressure.

13. The method according to claim 10, further comprising:
generating an acoustic and/or optical signal when there is a change in pressure.

14. The method according to claim 10, further comprising:
in the operating mode for detecting the recirculation, the substitute rate $Q_s$ is selected, at which a difference between the preset substituate rate $Q_s$ and a difference between the first blood flow rate $Q_{b1}$ and the second blood flow rate $Q_{b2}$ corresponds to a specific value.

15. The method according to claim 14, wherein the specific value is zero.

16. The method according to claim 10, further comprising:
calculating a ratio between an amount of the change in the pressure measured by the measuring unit in the arterial blood line and an amount of the change in the pressure measured in the venous blood line.

* * * * *